(12) United States Patent
Sharifzadeh et al.

(10) Patent No.: US 7,914,147 B2
(45) Date of Patent: Mar. 29, 2011

(54) SYSTEMS AND METHODS FOR OPTICAL DETECTION OF LIPOFUSCIN CONCENTRATIONS IN A SUBJECT'S EYE

(75) Inventors: Mohsen Sharifzadeh, Salt Lake City, UT (US); Werner Gellermann, Salt Lake City, UT (US)

(73) Assignee: Image Technologies Corporation, Salt Lake City, UT (US)

( * ) Notice: Subject to any disclaimer, the term of this patent is extended or adjusted under 35 U.S.C. 154(b) by 81 days.

(21) Appl. No.: 12/056,143

(22) Filed: Mar. 26, 2008

(65) Prior Publication Data
US 2009/0244484 A1 Oct. 1, 2009

(51) Int. Cl.
*A61B 3/10* (2006.01)
*A61B 3/00* (2006.01)
(52) U.S. Cl. .................. 351/213; 351/221; 351/246
(58) Field of Classification Search .................. 351/213, 351/221, 210, 246
See application file for complete search history.

(56) References Cited

U.S. PATENT DOCUMENTS

| | | |
|---|---|---|
| 6,205,354 B1 | 3/2001 | Gellermann et al. |
| 6,315,412 B1 | 11/2001 | Snodderly et al. |
| 2003/0004418 A1 | 1/2003 | Marmorstein |
| 2006/0082726 A1 | 4/2006 | Suzuki |
| 2006/0203194 A1 | 9/2006 | Suzuki |
| 2006/0244913 A1 | 11/2006 | Gellerman et al. |

OTHER PUBLICATIONS

J.R. Sparrow, C.A. Parish, M. Hashimoto, K. Nakanishi, "A2E, a Lipofuscin Fluorophore, in Human Retinal Pigmented Epithelial Cells in Culture," Investigative Ophthalmology & Visual Science, Nov. 1999, vol. 40, No. 12, pp. 2988-2995.

L. Hong, J. Garguilo, L. Anzaldi, G.S. Edwards, R.J. Nemanich, J.D. Simon, "Age-dependent Photoionization Threshold of Melanosomes and Lipofuscin Isolated from Human Retinal Pigment Epithelium Cells," Photochemistry and Photobiology, 2006, vol. 82, pp. 1475-1481.

F.C. Delori, D.G. Gorger, C.K. Dorey, "Age-Related Accumulation and Spatial Distribution of Lipofuscin in RPE of Normal Subjects," Investigative Ophthalmology & Visual Science, Jul. 2001, Vo. 42, No. 8, pp. 1855-1866.

S. Hayasaka, "Aging Changes in Lipofuscin, Lysomoes and Melanin in the Macular Are of Human Retina and Choroid," Japanese Journal of Ophthalmology, 1989, vol. 33, pp. 36-42.

F.C. Delori, M.R. Fleckner, D.G. Goger, J.J. Weiter, C.K. Dorey, "Autoflourescence Distribution Associated with Drusen in Age-Related Macular Degeneration," Investigative Ophthalmology & Visual Science, Feb. 2000, vol. 41, No. 2, pp. 496-504.

D. Yin, "Biochemical Basis of Lipofuscin, Ceroid, and Age Pigment-like Flourophores," Free Radical Biology & Medicine, 1996, vol. 21, No. 6, pp. 871-888.

R.F. Spaide, "Fundus Autofluorescence and Age-related Macular Degeneration," Ophthalmology, Feb. 2003, vol. 110, No. 2, pp. 392-399.

(Continued)

*Primary Examiner* — Jack Dinh
(74) *Attorney, Agent, or Firm* — Austin Rapp & Hardman

(57) ABSTRACT

A method for optical detection of lipofuscin concentrations in the retina is described. A subject's eye is exposed to a light source. Light emitted from the subject's eye is detected. Levels of lipofuscin are determined from the emitted light. A system for optical detection of lipofuscin in the retina is described. The system includes a light source to generate light. The system includes an optical detector in optical communication with the light source. The optical detector is configured to detect light emitted from a subject's eye. A computing device in electronic communication with the optical detector is included in the system to determine levels of lipofuscin from the emitted light.

13 Claims, 12 Drawing Sheets

OTHER PUBLICATIONS

F.C. Delori, C.K. Dorey, G. Staurenghi, O. Arend, D.G. Goger, J.J. Weiter, "In Vivo Flourescence of the Ocular Fundus Exhibits Retinal Pigment Epithelium Lipofuscin Characteristics," Investigative Ophthalmology & Visual Science, Mar. 1995, vol. 36, No. 3, pp. 718-729.

M. Sharifzadeh, P.S. Bernstein, W. Gellermann, "Nonmydriatic Flourescence-based Quantitative Imagine of Human Macular Pigment Distributions," Journal of the Optical Society of America, Oct. 2006, vol. 23, No. 10, pp. 2373-2387.

U. Wihlmark, A Wrigstad, K. Roberg, U.T. Brunk, S.E.G. Nilsson, "Lipofuscin formation in cultured retinal pigment epithelial cells exposed to photoreceptor outer segment material under different oxygen concentrations," APMIS, 1996, vol. 104 pp. 265-271.

N. Lois, A.S. Halfyard, A.C. Bird, F.W. Fitzke, "Quantitative evaluation of fundus autoflourescence imaged "in vivo" in eyes with retinal disease," British Journal of Ophthalmology, 2000, vol. 84, pp. 741-745.

F.C. Delori, "Spectrophotometer for noninvasive measurement of intrinsic fluorescence and reflectance of the ocular fundus," Applied Optics, Nov. 1994, vol. 33, No. 31, pp. 7439-7452.

J.R. Sparrow, K. Nakanishi, C.A. Parish, "The Lipofuscin Flourophore A2E Mediates Blue Light-Induced Damage to Retinal Pigmented Epithelial Cells," Investigative Ophthalmology & Visual Science, Jun. 2000, vol. 41, No. 7, pp. 1981-1989.

International Search Report issued for International Patent Application No. PCT/US09/38297on May 27, 2009.

International Preliminary Report on Patentability issued for International Patent Application No. PCT/US2009/038297on Oct. 7, 2010.

SYSTEMS AND METHODS FOR OPTICAL DETECTION OF LIPOFUSCIN CONCENTRATIONS IN A SUBJECT'S EYE

TECHNICAL FIELD

The present invention relates generally to optics and optical-related technology. More specifically, the present invention relates to systems and methods for optical detection of lipofuscin concentrations in a subject's eye.

BACKGROUND

Biological compounds may be used to determine information relating to a subject. For example, the presence of environmental toxins may be determined using biological compounds. Biological compounds may also be used to detect the presence of a disease. For example, the presence of antibodies may indicate that a disease has been detected by a subject's immune system.

Some biological compounds may be found in the skin and/or other areas of the body. Detection and measurement of biological compounds may require expensive equipment, long periods of time and/or other challenges. For example, detection of biological substances in the skin may require removing a sample and performing testing on the sample. Removing samples may cause a subject pain while testing may require that the sample be sent to a lab.

Lipofuscin is a compound found within the human retina. Lipofuscin compounds are generally yellowish pigments typically thought to arise from the progressive oxidation and/or glycation of proteins. In the healthy human body, lipofuscin is relatively uniformly distributed over the retina within the retinal epithelial layer ("RPE"). The formation of lipofuscin is generally thought to be associated with the role of the epithelial layer cells in phagocytosing the outer segment disc membranes that are typically shed daily by the photoreceptor cells. The loss of the outer segment membranes is irreversible since the human body does not replace the photoreceptor cells. Lipofuscin concentrations generally appear to be somewhat higher in the macular region of the retina than in the periphery.

Accordingly, lipofuscin may be used as a biological marker for aging of the human retina and, more generally, the human body. Therefore, benefits may be realized by providing systems and methods for detecting lipofuscin concentration levels in the human retina.

BRIEF DESCRIPTION OF THE DRAWINGS

Exemplary embodiments of the invention will become more fully apparent from the following description and appended claims, taken in conjunction with the accompanying drawings. Understanding that these drawings depict only exemplary embodiments and are, therefore, not to be considered limiting of the invention's scope, the exemplary embodiments of the invention will be described with additional specificity and detail through use of the accompanying drawings in which:

DETAILED DESCRIPTION

Figure 1:
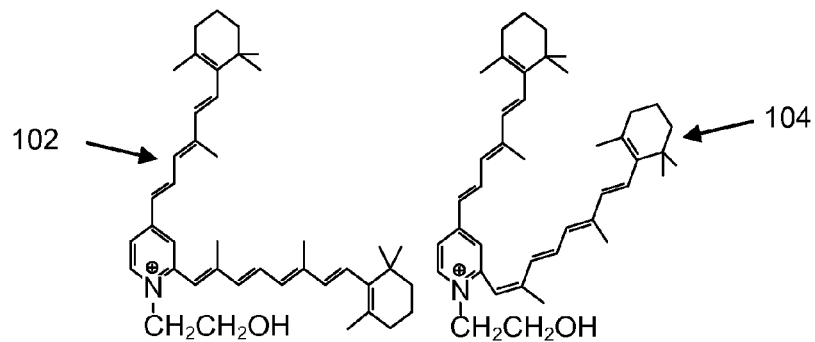
FIG. 1 illustrates the molecular structures of A2E and iso-A2E, the main constituents of lipofuscin.

A method for optical detection of lipofuscin concentrations in the retina is described. A subject's eye is exposed to a light source. The light source generates light at a wavelength that does not substantially overlap the absorption band of macular carotenoids. Light emitted from the subject's eye is detected. Levels of lipofuscin are determined from the emitted light. The subject's eye may be exposed to a fixation point.

Exposing the subject's eye to a light source may comprise directing the light to a desired portion of the subject's eye. Directing the light to a desired portion of the subject's eye may comprise directing the light to the macular region of the subject's eye. Directing the light to a desired portion of the subject's eye may also comprise directing the light to an off-macular region of the subject's eye. The off-macular region may be selected from the group consisting of a nasal portion, a temporal portion, a superior portion or an inferior portion.

Detecting light emitted from the subject's eye may comprise filtering the light emitted from the subject's eye. Filtering the light emitted from the subject's eye may comprise using a long pass filter at about 665 nm.

The lipofuscin levels may be compared to correlative data indicative of changes of lipofuscin levels in a subject's eye over time due to the uptake of nutritional supplements or drugs.

A system for optical detection of lipofuscin concentrations in the retina is also described. The system includes a light source to generate light. The light generated by the light source is at a wavelength that substantially overlaps the absorption band of lipofuscin but does not substantially overlap the absorption band of macular carotenoids. The system includes an optical detector in optical communication with the light source. The optical detector is configured to detect light emitted from a subject's eye. A computing device is in electronic communication with the optical detector and is configured to determine levels of lipofuscin from the emitted light.

In one configuration, the light source may generate light at a wavelength of about 532 nm. An optical element may also be included to direct the light to a desired portion of the subject's eye.

The system may also include an optical filter in optical communication with the optical detector and the subject's eye. The optical filter may comprise a long pass filter at about 665 nm.

A system for optical detection of lipofuscin concentrations in the retina is also described. The system includes a light source to generate light and an optical element in optical communication with the light source. The optical element is configured to direct the light to a desired portion of the subject's eye. An optical detector is in optical communication with the light source. The optical detector is configured to detect light emitted from a subject's eye. A computing device is in electronic communication with the optical detector and is configured to determine levels of lipofuscin from the emitted light.

Various embodiments of the invention are now described with reference to the Figures, where like reference numbers indicate identical or functionally similar elements. The embodiments of the present invention, as generally described and illustrated in the Figures herein, could be arranged and designed in a wide variety of different configurations. Thus, the following more detailed description of several exemplary embodiments of the present invention, as represented in the Figures, is not intended to limit the scope of the invention, as claimed, but is merely representative of the embodiments of the invention.

The word "exemplary" is used exclusively herein to mean "serving as an example, instance, or illustration." Any embodiment described herein as "exemplary" is not necessarily to be construed as preferred or advantageous over other embodiments.

Some features of the embodiments disclosed herein may be implemented as computer software, electronic hardware, or combinations of both. To clearly illustrate this interchangeability of hardware and software, various components may be described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Where the described functionality is implemented as computer software, such software may include any type of computer instruction or computer executable code located within a memory device and/or transmitted as electronic signals over a system bus or network. Software that implements the functionality associated with components described herein may comprise a single instruction, or many instructions, and may be distributed over several different code segments, among different programs, and across several memory devices.

As used herein, the terms "an embodiment", "embodiment", "embodiments", "the embodiment", "the embodiments", "one or more embodiments", "some embodiments", "certain embodiments", "one embodiment", "another embodiment" and the like mean "one or more (but not necessarily all) embodiments of the disclosed invention(s)", unless expressly specified otherwise.

The term "determining" (and grammatical variants thereof) is used in an extremely broad sense. The term "determining" encompasses a wide variety of actions and therefore "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

Lipofuscin is commonly thought to be an indicator of oxidative stress and tissue aging, and is sometimes referred to as a "wear and tear pigment". There is increasing evidence that lipofuscin compounds are toxic and that the accumulation of lipofuscin is directly correlated with tissue aging and diseases such as diabetes and age-related macular degeneration.

Light irradiation of cell cultures appears to accelerate the formation of lipofuscin. Also, the formation of lipofuscin may be nearly eliminated in oxygen-free conditions. Furthermore, the formation of lipofuscin has been observed to generally increase with vitamin E deficiency. These findings may support the hypothesis that lipofuscin formation may be associated with light-induced oxidative stress of the tissue as well as oxidation products caused by metabolic mechanisms. Lipofuscin levels can vary significantly between different human subjects and therefore may give an indication of the tissue aging in individuals. Lower levels of lipofuscin may therefore be desirable and lipofuscin levels may be reduced via dietary intervention strategies, nutritional supplementation, drugs, and/or reduction of external oxidative stress factors such as smoking.

In one embodiment, an optical detection method for lipofuscin levels in a subject's eye is described. In another embodiment, a portable, field-usable apparatus that allows one to rapidly quantify lipofuscin levels in human subjects and to track their levels over time is described. The optical detection of lipofuscin in a subject's eye may be of particular interest to the nutritional supplement industry where the formation of the lipofuscin "wear and tear" biomarker may be monitored over time and/or may be potentially reduced via supplementation. The systems and methods disclosed may also be of interest to medical sciences such as Ophthalmology and Epidemiology where they may provide a research tool useful in investigating the correlation between lipofuscin and diseases in large subject populations.

In the present embodiment, the systems and methods may optically detect lipofuscin in a human eye. In other embodiments, the systems and methods may optically detect lipofuscin in any subject's eye. For example, the systems and methods may optically detect lipofuscin in mice or in a canine eye.

As discussed above, the RPE may contain the pigment lipofuscin. Lipofuscin may accumulate in the lysosomal body of the RPE cells. A major fluorophore of lipofuscin compounds is a molecule termed A2E. This molecule is strongly fluorescent and therefore is amenable to detection by non-invasive and rapid optical means. The molecular structures of A2E 102 and its isomer, iso-A2E 104, are shown in FIG. 1. A2E 102 and iso-A2E 104 may absorb strongly in the blue wavelength region and may emit strongly in the orange-red region. As shown in FIG. 1, A2E 102 and iso-A2E 104 are two isomers of a bis-substituted pyridinium ring.

Figure 2:
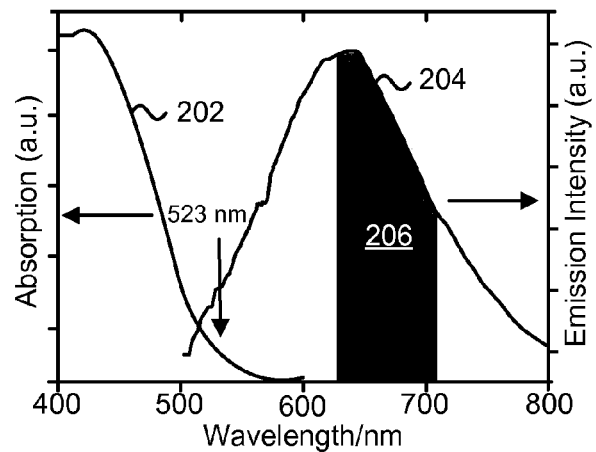
FIG. 2 illustrates the absorption and emission spectra of a methanolic solution of A2E.

FIG. 2 illustrates the absorption and emission spectra of a methanolic solution of A2E. The absorption spectrum 202 of A2E typically occurs in a broad band in the blue wavelength range, with a maximum near about 430 nm. The absorption spectrum 202 of A2E generally extends well beyond about 500 nm into the green wavelength range. The emission spectrum 204 typically occurs in a broad band from the green wavelength range (about 500 nm) into the infrared wavelength range (more that about 800 nm). The emission spectrum 204 is generally centered at about 660 nm.

Care may be taken in fluorescence spectroscopy to avoid confounding influences of unwanted optical signals in the detection of the compound of interest. In the case of lipofuscin detection there may be potentially confounding influences from macular pigments and from fluorescence of the human lens. Macular pigments typically absorb in the blue wavelength region (peak at about 460 nm).

The influence of macular pigments may be reduced by choosing an excitation wavelength that is just outside the absorption of macular pigment but still overlapping the lipofuscin absorption on its long-wavelength shoulder, in the green wavelength region. For example, the excitation wavelength may be about 532 nm.

Reducing the influence of macular pigment may include measuring lipofuscin levels at retinal locations outside the macular region. Macular pigment levels are typically an order of magnitude lower outside the macular region than in the macular region. Regions outside the macular region may include the temporal, nasal, superior and/or inferior positions.

For example, while the subject's eye fixates on an adjustable aiming beam, the lipofuscin content of peripheral retinal regions may be measured. Besides avoiding the influence of macular pigments, this scheme also reduces cone photoreceptor bleaching, since the cone photoreceptor concentrations are significantly lower in the peripheral regions. This may prevent the occurrence of strong after images in the measurements, which otherwise may be caused by temporary bleaching of the cone photoreceptors.

The influences of lens fluorescence may be reduced by limiting the lipofuscin fluorescence detection to wavelengths beyond the wavelength region where lens fluorescence ceases to exist. For example, lipofuscin fluorescence detection may be limited by the limited emission curve 206 between about 600 nm and about 700 nm, in the present embodiment. In this range, the peak of the lipofuscin emission spectrum 204 may be detected without interference from lens fluorescence and/or other interference. In other embodiments, the limited emission curve 206 may include a wider range of wavelengths, or a wavelength range limited to the long-wavelength shoulder of lipofuscin emission band.

Figure 3:
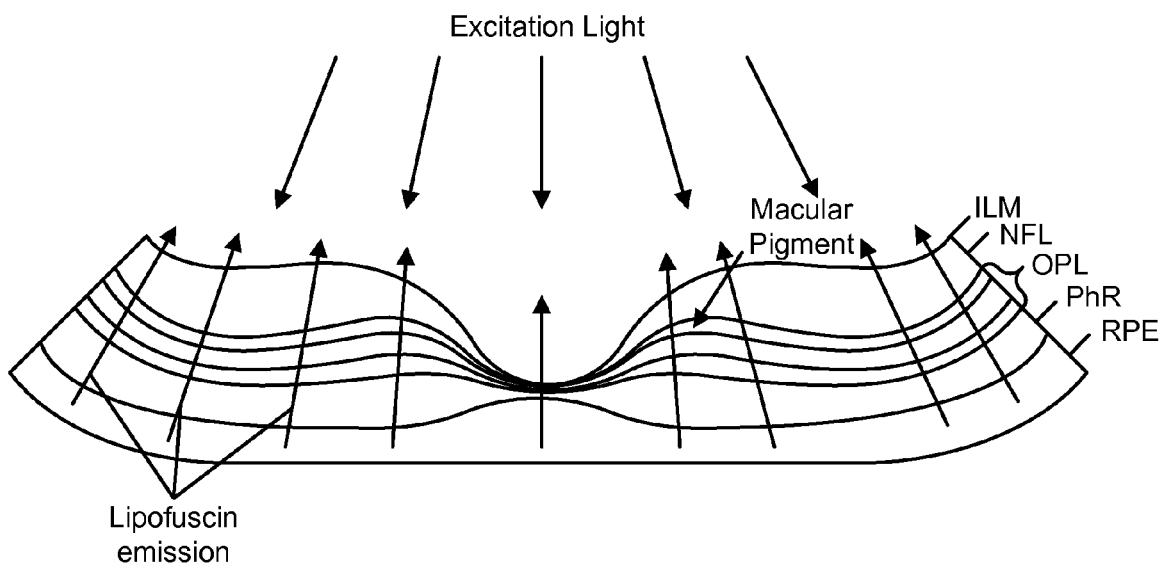
FIG. 3 is a schematic representation of retinal layers participating in light absorption, transmission, and scattering of excitation and emission light in a portion of the retina.

FIG. 3 is a schematic representation of retinal layers participating in light absorption, transmission, and scattering of excitation and emission light in a portion of the retina. The retinal layers include the ILM (the inner limiting membrane), the NFL (the never fiber layer), the OPL (the outer photoreceptor layer), the PhR (the photoreceptor layer), and the RPE (the retinal pigment epithelium). In order to avoid excitation of the macular pigments found in the macular region of the retina, lipofuscin levels may be measured with excitation wavelengths lying outside the absorption range of macular pigments, shown in FIG. 3 as shaded area in the outer photoreceptor layer. As an additional preventive measure, lipofuscin levels may be measured outside of the macular region. Excitation of lipofuscin in the long wavelength region may excite fluorescence of lipofuscin located in the RPE layer of the retina. The combination of long-wavelength excitation and/or detection of the fluorescence on the long-wavelength shoulder may permit selective detection of lipofuscin without confounding absorption and/or fluorescence from anterior ocular media.

Figure 4:
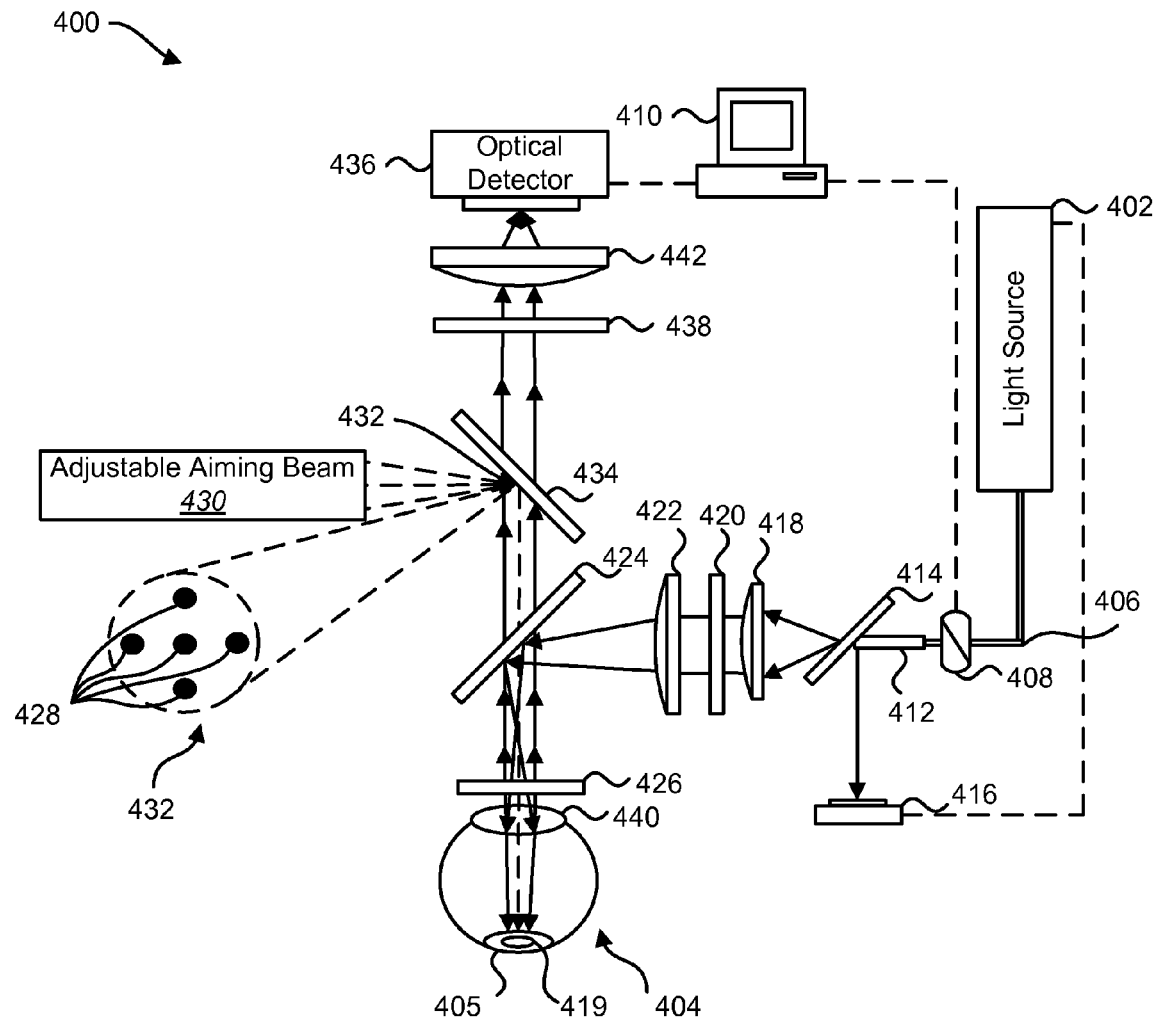
FIG. 4 is a functional block diagram illustrating an embodiment of a system for optical detection of lipofuscin in a subject's eye.

FIG. 4 is a functional block diagram illustrating an embodiment of a system 400 for optical detection of lipofuscin in a subject's eye. The system 400 may include a light source 402. The light source 402 may generate light that may be directed to a subject's eye 404.

The light may be generated at a wavelength that substantially overlaps the absorption band of lipofuscin but does not substantially overlap the absorption band of macular carotenoids. In the present embodiment, the light may be generated at a wavelength of about 532 nm. In other embodiments, the light may be generated at wavelengths encompassing about 532 nm. The choice of this 532 nm wavelength also has an advantage in that it lies outside the absorption range of potential lens absorption effects caused by the pigmentation of cataracts.

In further embodiments, the light may be generated at wavelengths that may substantially overlap the absorption band of macular carotenoids. In embodiments where the light is generated at wavelengths that may substantially overlap the absorption band of macular carotenoids, the lipofuscin levels may be measured generally outside of the macular region.

The light source 402 may be a light emitting diode (LED) light source. The light source 402 may include a laser light source, an LED light source, a conventional light source, and/or other light sources. For example, a low-cost LED light source may be used, that is projected as a large (5 mm diameter) spot onto the retina. A conventional light source may require suitable filtering to provide the desired light characteristics. In the present embodiment, only one light source may be used. In other embodiments, multiple light sources may be used.

The light source 402 may be in optical communication with one or more optical components. The optical components may direct the light generated by the light source 402 to the subject's eye 404. An optical fiber 406 may be used to direct the light generated by the light source 402. The light source 402 may also be coupled directly into the eye without the use of a fiber. A shutter 408 may be used to prevent optical communication between the generated light and the subject's eye 404. In the present embodiment, the shutter 408 may provide a well defined light exposure time of about 200 milliseconds (msec). In other embodiments, longer or shorter exposure times may be used. The shutter 408 may be controlled by a computing device 410. In the present embodiment, the computing device 410 may be a personal computer. In other embodiments, the computing device 410 may include other computing devices.

When the shutter 408 permits optical communication between the generated light and the subject's eye 404, the generated light may be in optical communication with an optical probe head 412. The optical probe head 412 may communicate the light to a first beam splitter 414. The first beam splitter 414 may be positioned at an angle of incidence of about 45 degrees to the light source 402 (i.e. to the light emitted from the light source 402). The first beam splitter 414 may be used to direct a portion of the generated light to a first optical detector 416. The first optical detector 416 may be used for feedback control. The computing device 410 may be in electronic communication with the first optical detector 416. The first beam splitter 414 may direct another portion of the generated light to a first lens 418.

The first lens 418 may condition the light to create a target spot 419. For example, the first lens 418 may enlarge and/or reduce the light to a predetermined size and/or shape on the subject's retina 405. In the present embodiment, the first lens 418 may expand the light to create about a 1 cm disk shaped target 419. In other embodiments, the first lens 418 may expand and/or reduce the light to a target 419 with other predetermined shapes and/or areas. For example, the first lens 418 may expand and/or reduce the light to predetermined shapes such as an ellipse, an annulus, a polygon, multiple ellipses and/or other predetermined shapes. In another example, the first lens 418 may expand and/or reduce the light to predetermined areas such as about 157 square pixels, about 314 square pixels, about 471 square pixels, about 628 square pixels, and/or other predetermined areas. A predetermined shape, such as a circle, may have a diameter of about 50 pixels, such that the predetermined area may be about 157 square pixels.

The light may be communicated to a first filter 420. In the present embodiment, the first filter 420 may be a narrow band pass filter. In other embodiments, the first filter 420 may be a laser line filter.

The system 400 may include a second lens 422. The light may be directed through the second lens 422. The second lens 422 may be used to direct the light into the subject's eye 404. In the present embodiment, the second lens 422 may direct the shaped and/or sized light target 419 into the retina 405 of the subject's eye 404. The second lens 422 may direct the light to a second beam splitter 424. In the present embodiment, the second beam splitter 424 may be a dichroic holographic beam splitter. The second beam splitter 424 may be used to reflect the light into the subject's eye 404.

The light may pass through an aperture 426 before contacting the subject's eye 404. The aperture 426 may be positioned in front of the subject's eye 404. The aperture 426 may be used to block reflections originating from the second beam splitter 424.

A fixation point 428 may be used to position the subject's eye 404, i.e. the exact retinal location to which the excitation beam is directed. It can be any location in the retina, centered onto the macula, or centered onto a region off the macula. The fixation point 428, in the present embodiment, may be generated by an adjustable aiming beam generator 430. In the present embodiment, the fixation point 428 may include a fixation target 432. For example, the fixation target 432 may include multiple fixation points 428 in a cross-hairs configuration to facilitate fixation of the subject's eye 404. The fixation point 428 may be in optical communication with the subject's eye 404. FIG. 4 illustrates the fixation target 432, and a close-up view of the fixation target 432 showing one embodiment of fixation points 428.

In the present embodiment, the fixation point 428 may be in optical communication with a third beam splitter 434. The third beam splitter 434 may be positioned at an angle of incidence of about 45 degrees to the subject's eye 404. The third beam splitter 434 may reflect the fixation point 428 into the subject's eye 404. The fixation point 428, in the present embodiment, may pass through the second beam splitter 424 and/or the aperture 426 into the subject's eye 404. In the present embodiment, the subject's eye 404 may be fixated before the light is directed into the subject's eye 404. For example, the shutter 408 may not activate until the subject's eye 404 is fixated.

The subject's eye 404 may be in optical communication with a second optical detector 436. A portion of the light may be absorbed by the subject's eye 404. A portion of the light may be emitted by the subject's eye 404. For example, the lipofuscin in the retina 405 may emit light. The emitted light may pass through the aperture 426. The emitted light may pass through the second beam splitter 424. For example, the second beam splitter 424 may be transparent for desired wavelengths. In the present embodiment, the second beam splitter 424 may be a long pass filter at about 600 nm. In another embodiment, the second beam splitter may be a long pass filter at about 650 nm. The second beam splitter 424 may be positioned at an angle of incidence of about 45 degrees to the light source 402 (i.e. to the light emitted from the light source 402).

The emitted light may pass through the third beam splitter 434. A second filter 438 may be in optical communication with the subject's eye 404 and/or the second optical detector 436. The second filter 438 may be used to prevent fluorescence emitted from the lens 440 of the subject's eye 404 from being detected by the second optical detector 436. The second filter 438 may further be used to prevent fluorescence from melanin in the subject's eye 404. In the present embodiment, the second filter 438 may include a long pass filter at about 665 nm. In another embodiment, the second filter 438 may include a long pass filter at about 690 nm. In a further embodiment, the second filter 438 may include a long pass filter at about 670 nm. In another further embodiment, the second filter 438 may include a band pass filter centered at about 670 nm.

A third lens 442 may be in optical communication with the second optical detector 436 and/or the subject's eye 404. The third lens 442 may image the emitted light onto the second optical detector 436.

The second optical detector 436 may detect the light emitted from the subject's eye 404. For example, the second optical detector 436 may measure the intensity of the light emitted from the subject's eye 404. The second optical detector 436 may include a CCD camera, a photomultiplier tube, a photodiode detector and/or other optical detectors. In some embodiments, the second optical detector 436 may include a spatially integrating optical detector.

The second optical detector 436 may be in electronic communication with the computing device 410. The second optical detector 436 may convert the detected light into an electronic signal. The electronic signal may be sent to the computing device 410. The computing device 410 may be used to determine levels of lipofuscin in the subject's eye 404. Determining levels of lipofuscin in the subject's eye 404 may include processing the electronic signal from the second optical detector 436. Processing the electronic signal from the second optical detector 436 may include analyzing and/or visually displaying the signal on a monitor (not shown) and/or other display. Processing the electronic signal from the second optical detector 436 may further include converting the light signal into other digital and/or numerical formats. Data acquisition software may be used by the computing device 410 to determine the levels of lipofuscin in the subject's retina 405.

In the present embodiment, one measurement of the lipofuscin levels in the subject's retina 405 may be made for a relatively large excitation disk such that the lipofuscin levels are averaged over that disk. In other embodiments, multiple measurements may be taken. In embodiments where multiple measurements of lipofuscin levels may be taken, the multiple measurements may be averaged to determine an average lipofuscin level for the subject. In some embodiments where the lipofuscin levels may be averaged, the measurements may be taken from the same location in the subject's retina 405. For example, light used for each measurement may be directed to the same portion of the retina 405. In other embodiments, measurements may be taken from the different locations in the subject's retina 405. For example, light used for each measurement may be directed to the different portions of the retina 405. In further embodiments, a combination of measurements from the same and/or different locations may be used to determine the average lipofuscin levels in a subject's retina 405.

In some embodiments, directing light to a portion of the retina 405 of the subject's eye 404 may be accomplished by having the subject fixate on the aiming target such that the light is directed to a desired portion of the retina 405. For example, the second lens 422 may be positioned to direct the light to a desired portion of the retina 405. In the present embodiment, the light is shown on the subject's eye 404 as the target 419 located in the macular region of the retina 405. In other embodiments, the light (i.e. target 419) may be directed onto other portions of the subject's retina 405.

Figure 4A:
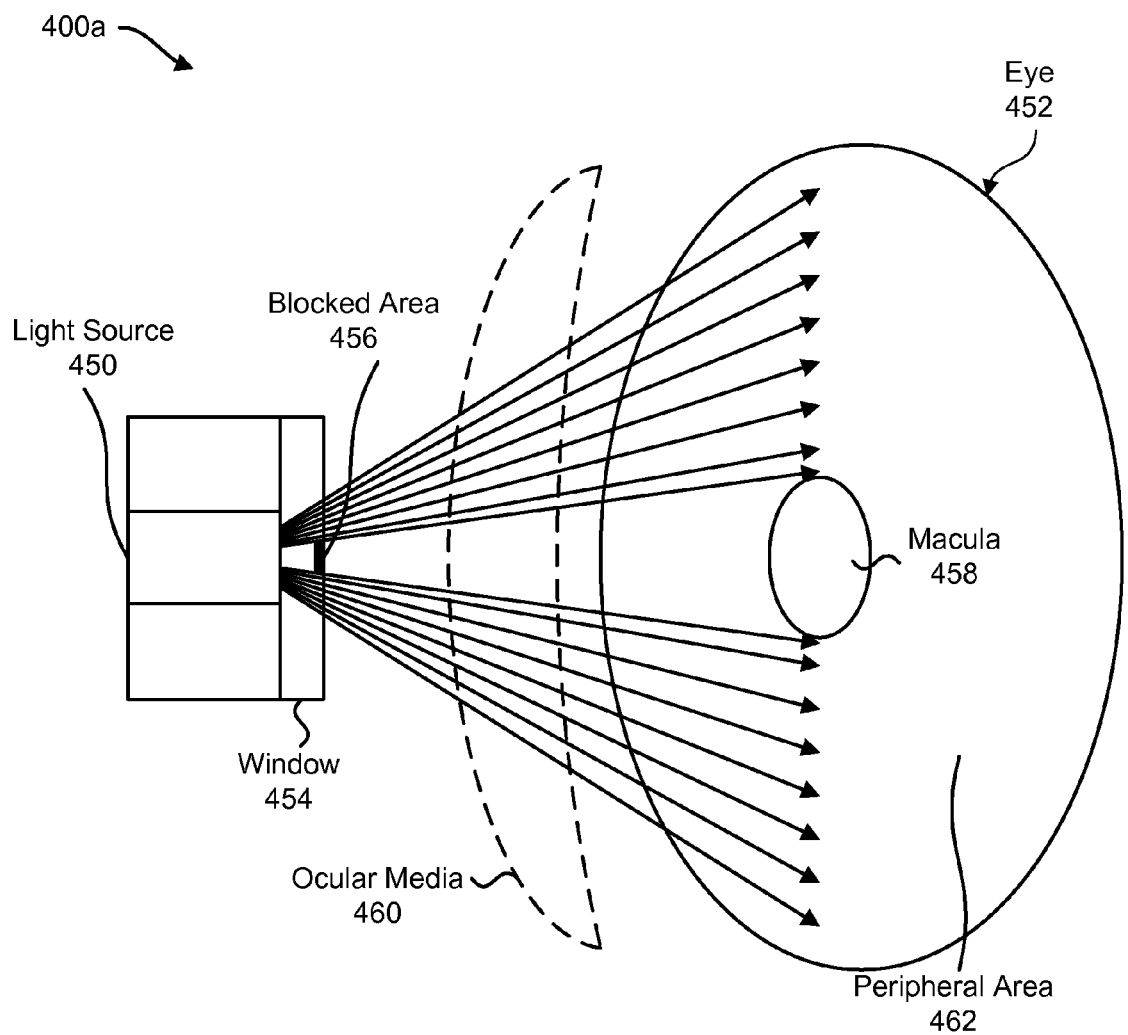
FIG. 4a is a simplified functional block diagram illustrating an embodiment of a system for optical detection of lipofuscin in a subject's eye.

FIG. 4a is a simplified functional block diagram illustrating an embodiment of a system 400a for optical detection of lipofuscin in a subject's eye. The system 400a may include a light source 450. The light source 450 may generate light that may be directed to a subject's eye, more specifically the retina 452. The light from the light source 450 may pass through a window 454 towards the eye 452. The window 454 may include a blocked area 456. The blocked area 456 may substantially block the light from exposing the macula region 458. The light passes through the window 454 to the peripheral retinal area 462. The light may also pass through ocular media 460.

Figure 5:
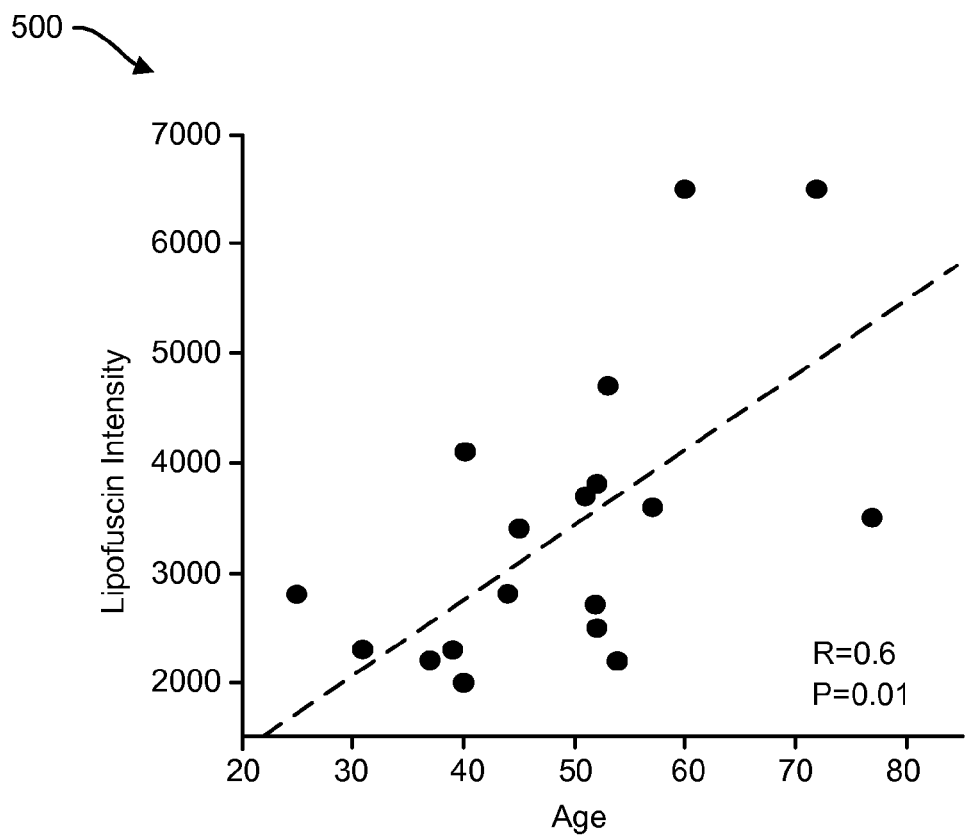
FIG. 5 illustrates a graph generally indicating the age dependence and inter-subject variation of retinal lipofuscin levels.

FIG. 5 illustrates a graph 500 generally indicating the age dependence and inter-subject variation of retinal lipofuscin levels. In the present graph 500, retinal lipofuscin levels were measured for eighteen healthy human subjects of which eleven were male and seven female. The data points represent lipofuscin levels obtained from CCD camera images under 532 nm excitation. The levels generally indicate a significant increase in lipofuscin intensity with respect to age. Large concentration differences may exist between individuals. In the present graph 500, the concentration differences are about ten-fold. These concentration differences that may exist between individuals may indicate different degrees of tissue aging. Therefore, it may be desirable to measure the lipofuscin intensity of a subject's eye 404 in order to determine the degree of tissue aging in the subject.

Measuring the lipofuscin intensity of a subject's retina 405 may provide further benefits. For example, if multiple measurements are made over time, these measurements may be used to monitor the subject's response to dietary intervention strategies, nutritional supplementation, drugs, reduction of external oxidative stress factors such as smoking and/or other factors. Additionally, measuring the lipofuscin intensity of a subject's retina 405 may provide a research tool for investigating the correlation between lipofuscin and diseases in large subject populations.

Figure 5A:
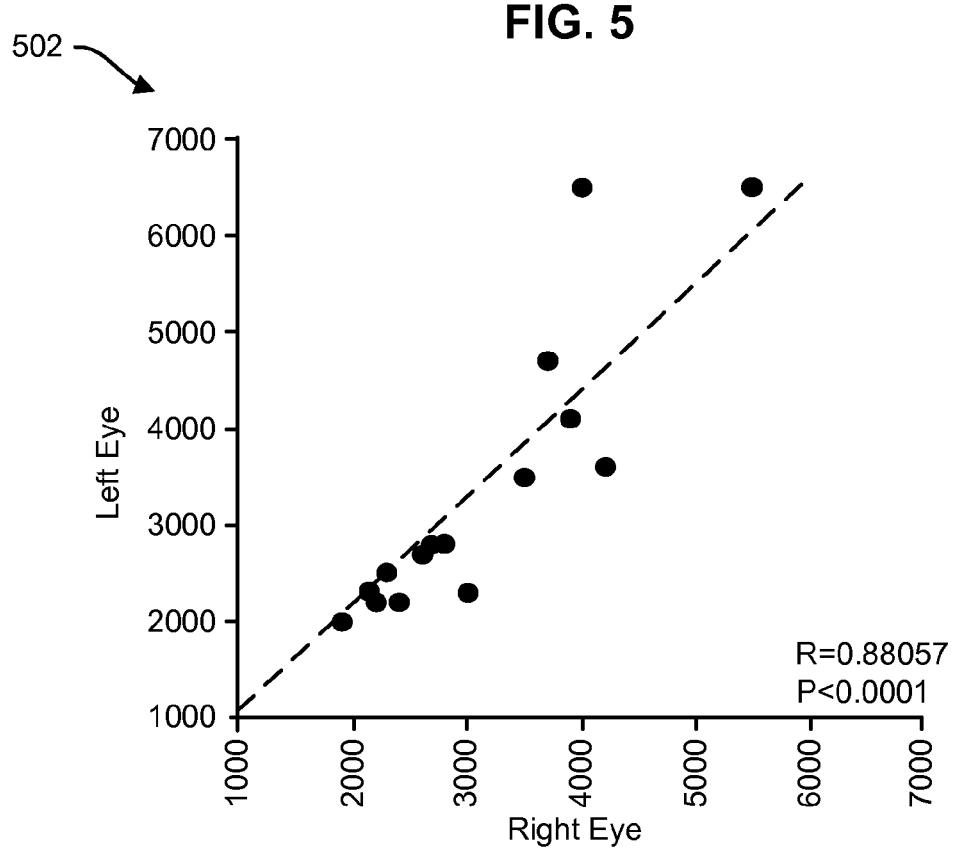
FIG. 5a illustrates a graph generally indicating the left eye-right eye correlation of lipofuscin intensity.

FIG. 5a illustrates a graph 502 generally indicating the correlation of both eyes and lipofuscin intensity. The graph 502 shows a high left eye-right eye correlation of lipofuscin intensity.

Figure 6:
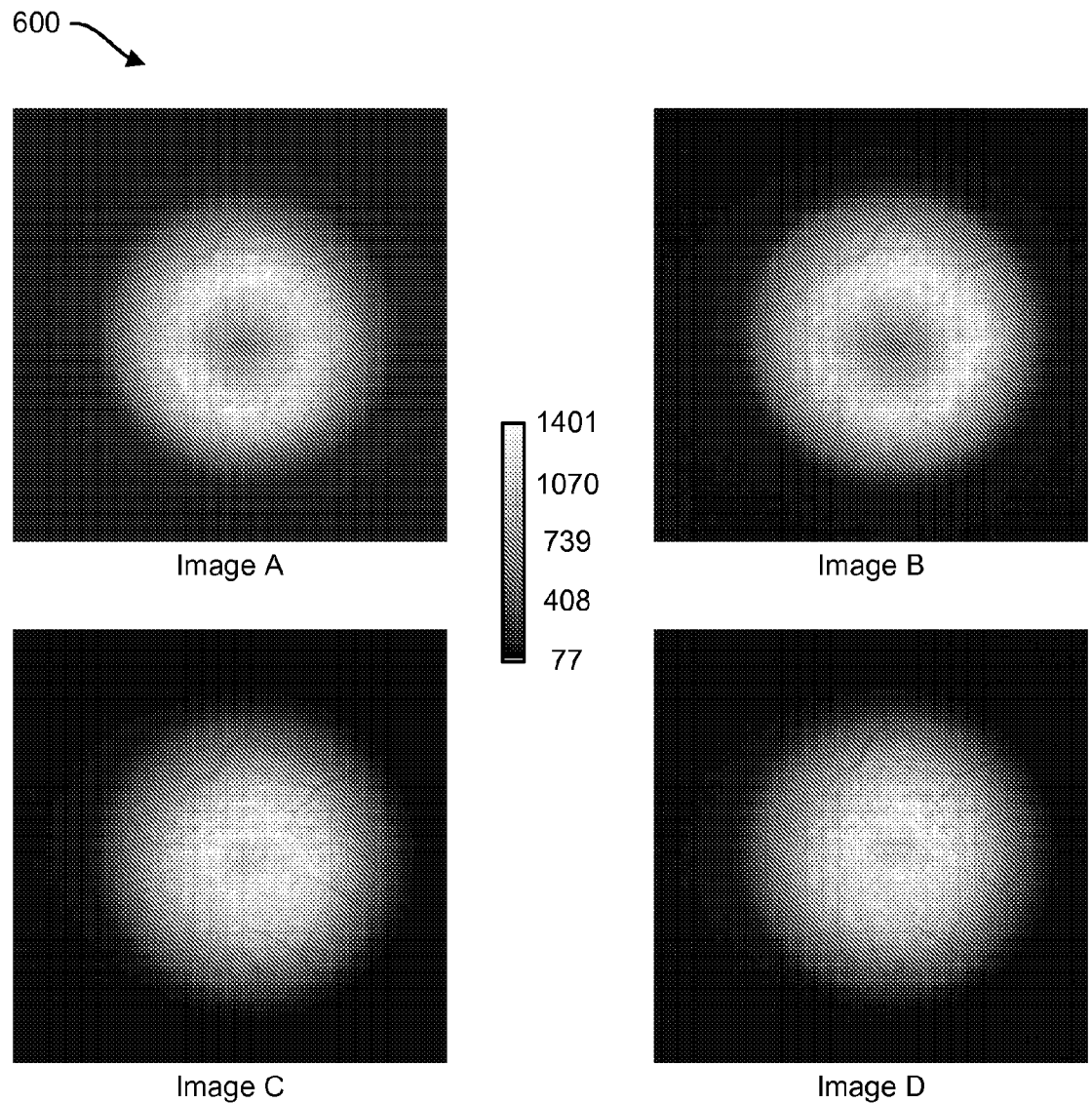
FIG. 6 illustrates gray-scale CCD camera images for four different subjects, obtained at lipofuscin detection wavelengths above about 665 nm, and excitation at 532 nm.

FIG. 6 illustrates gray-scale CCD camera images 600 obtained at lipofuscin detection wavelengths above about 665 nm. Image A and Image B were obtained with an excitation wavelength at about 488 nm. Image C and Image D were obtained with an excitation wavelength at about 532 nm. The intensity levels of lipofuscin are coded in gray-scale. Under 488 nm excitation, shown in Images A and B, a strong attenuation of the lipofuscin response may be caused by macular pigment. Under 532 nm excitation, shown in Images C and D, the macular pigment absorption may be significantly reduced, resulting in images that are spatially uniform in lipofuscin intensity levels. In order to avoid the attenuation of the lipofuscin response that may be caused by the macular pigment, it may be desirable to provide a light source that is nearer in wavelength to about the 532 nm range than the 488 nm range.

Figure 7:
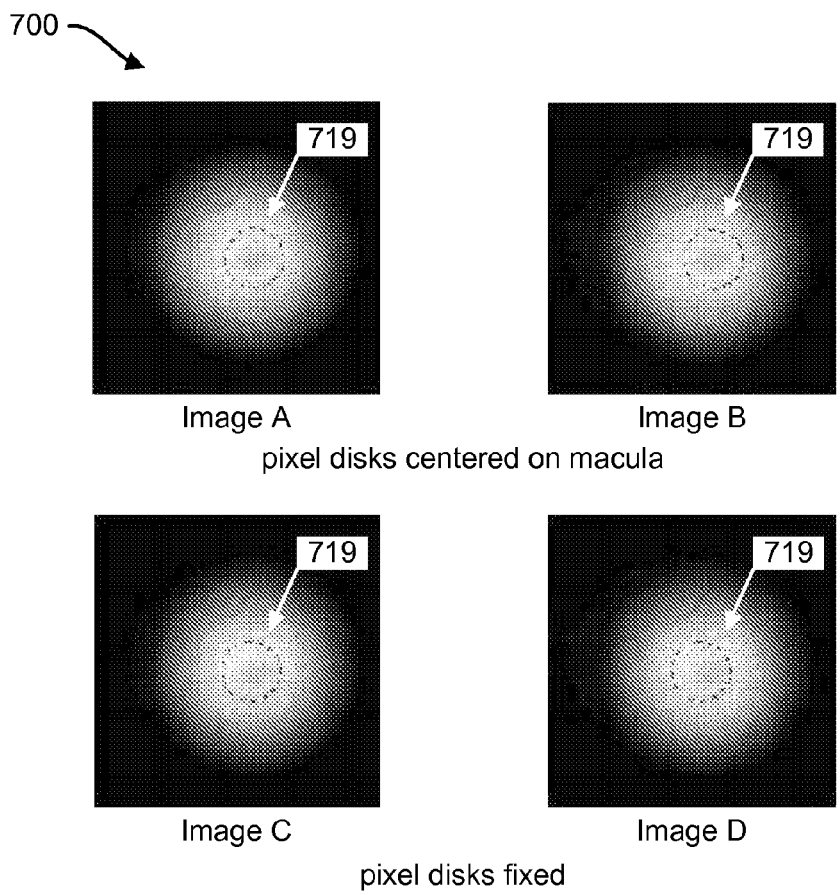
FIG. 7 illustrates retinal images obtained for optical detection of lipofuscin at detection wavelengths above 665 nm and excitation at 532 nm in a subject's eye.
Figure 8:
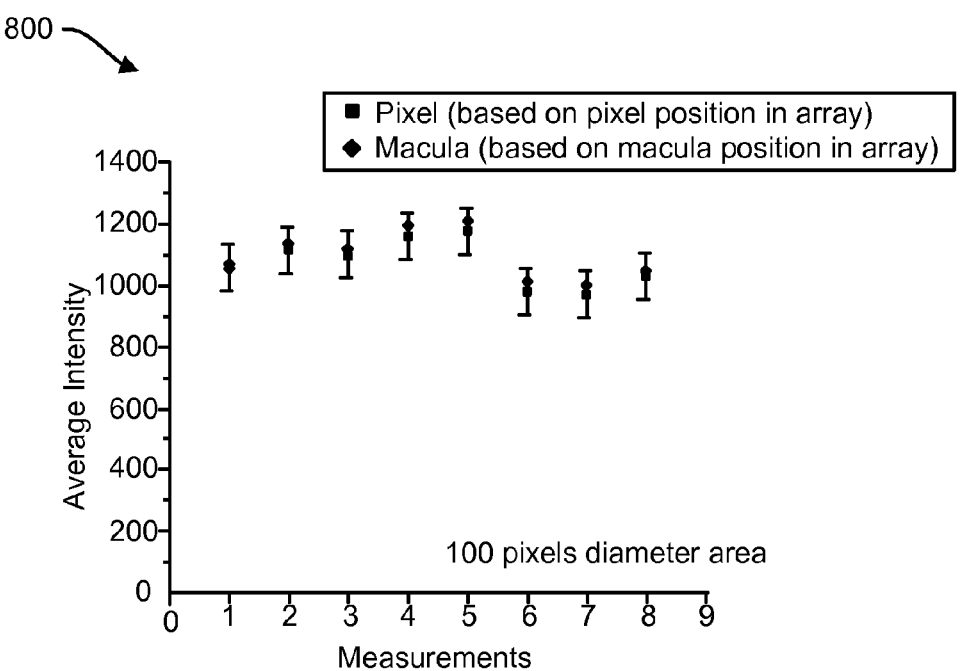
FIG. 8 illustrates a graph indicating the average intensity of lipofuscin levels obtained in eight successive measurements without centering the aiming target onto the macula.

FIG. 7 illustrates retinal images 700 obtained for optical detection of lipofuscin in a subject's retina 405 obtained with light excitation at 532 nm, and for the case where the macula is fixating on the aiming beam, i.e. a case where the lipofuscin intensities of the retina are measured in the macular region. FIG. 8 illustrates a graph 800 indicating the average intensity of lipofuscin levels obtained with two different processing methods In the present images, a pixel area 719 with a predetermined disk shape having a 100 pixel diameter (resulting in a predetermined area of about 314 square pixels) is chosen (dashed-line circles). In one of the two processing methods, images A and B were processed by centering the pixel area 719 onto the macula. Typically, the alignment of the macula onto the fixating aiming beam is not perfect. Therefore, the exact position of the macula shifts sufficiently from image to image such that a corresponding centering of the evaluation pixel areas 719 may be necessary for each measurement. In the second processing method, images C and D were processed by keeping the pixel area 719 intentionally fixed at a predetermined location. In this case, the pixel area 719 may not necessarily be centered on the macula. However, comparing the results of both methods generally indicates that similar levels are obtained using both methods. This is further exemplified in FIG. 8, where the results of average lipofuscin intensities are plotted for a total of eight measurements using both processing methods. Again, the results are very similar. Therefore, it may be sufficiently accurate to use fixed pixel area locations rather than centering the pixel areas for each measurement onto the macula or any other targeted area of the retina.

In the present embodiment, pixel areas 719 with a predetermined disk shape are used to measure the lipofuscin levels in the subject's retina 405. In other embodiments, varying pixel area shapes and/or sizes may be used to measure the lipofuscin levels in the subject's retina 405.

Figure 9:
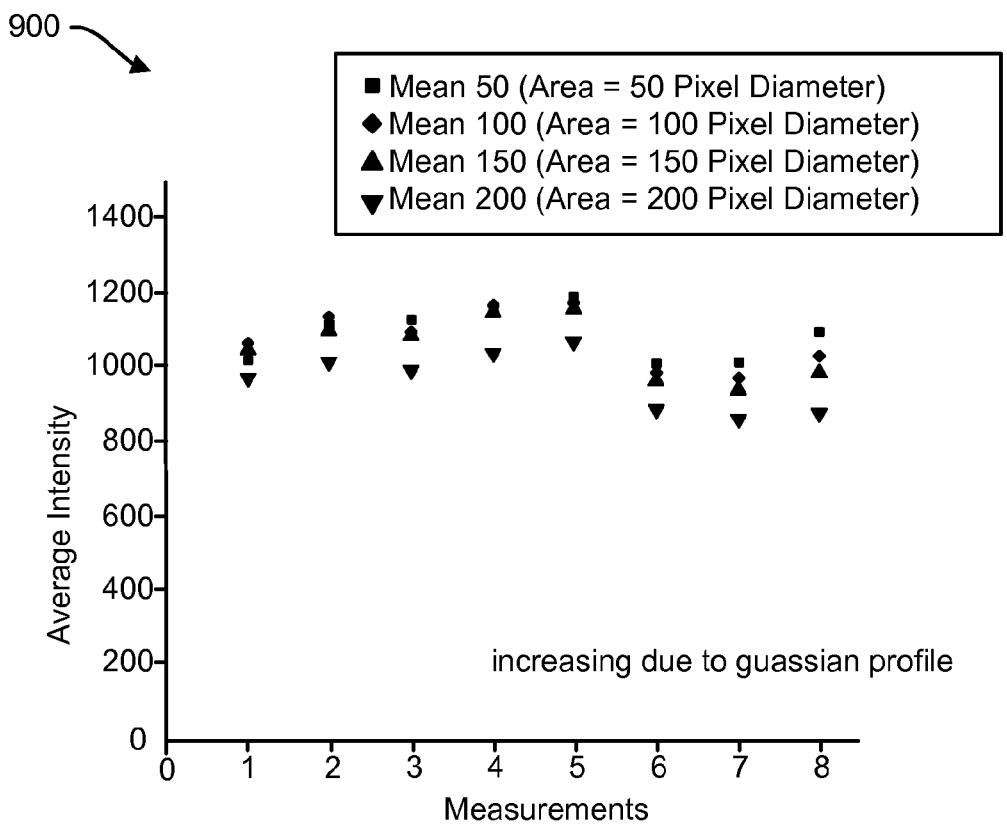
FIG. 9 illustrates a graph indicating the average intensity of lipofuscin levels with varying predetermined target area sizes.

FIG. 9 illustrates a graph 900 indicating the average intensity of lipofuscin levels with varying pixel areas used for processing. In the present embodiment, the areas 419 may have a predetermined disk shape. In other embodiments, the areas 419 may have predetermined shapes such as an ellipse, an annulus, a polygon, multiple ellipses and/or other predetermined shapes. In the present embodiment, the disk shaped areas 419 have diameters of about 50, about 100, about 150 and about 200 pixels, respectively. Based on these diameters, the areas 419 may have predetermined areas of about 157 square pixels, about 314 square pixels, about 471 square pixels and about 628 square pixels, respectively. In other embodiments, other predetermined areas may be used. This graph 900 generally indicates that lipofuscin intensities are mainly constant with regard to the evaluating pixel area size. The lipofuscin intensities appear to increase only slightly with decreasing areas. This increase may be due to the Gaussian intensity distribution of the excitation spots, which may have higher intensities in the center of the spots compared to the perimeter.

Figure 10:
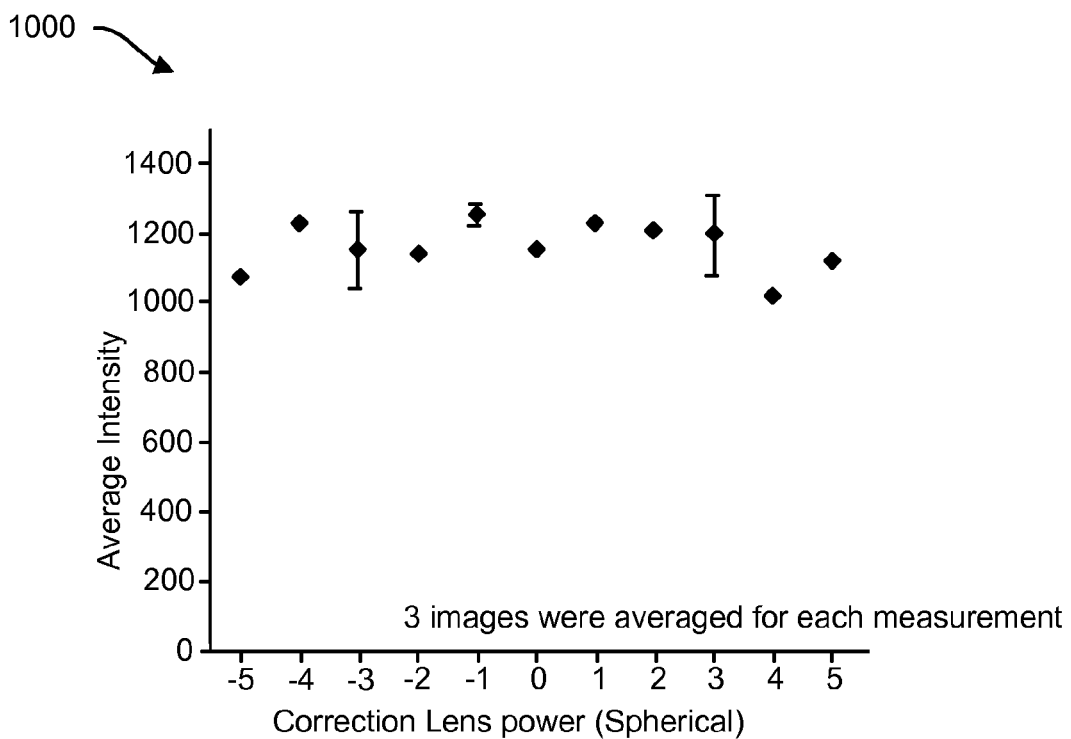
FIG. 10 illustrates a graph indicating the nearly constant average intensity of lipofuscin levels obtained when using varying correction lens power.

FIG. 10 illustrates a graph 1000 indicating the average intensity of lipofuscin levels with varying correction lens powers the subject may use to correct his eye sight. In the present graph 1000, a spherical correction lens was used. The correction lens power varied from −5 to +5. These measurements may generally indicate roughly constant levels of lipofuscin independent of lens correction. Therefore, it may not be necessary to use a correction lens in the present embodiment. In other embodiments, a correction lens may be used.

Figure 11:
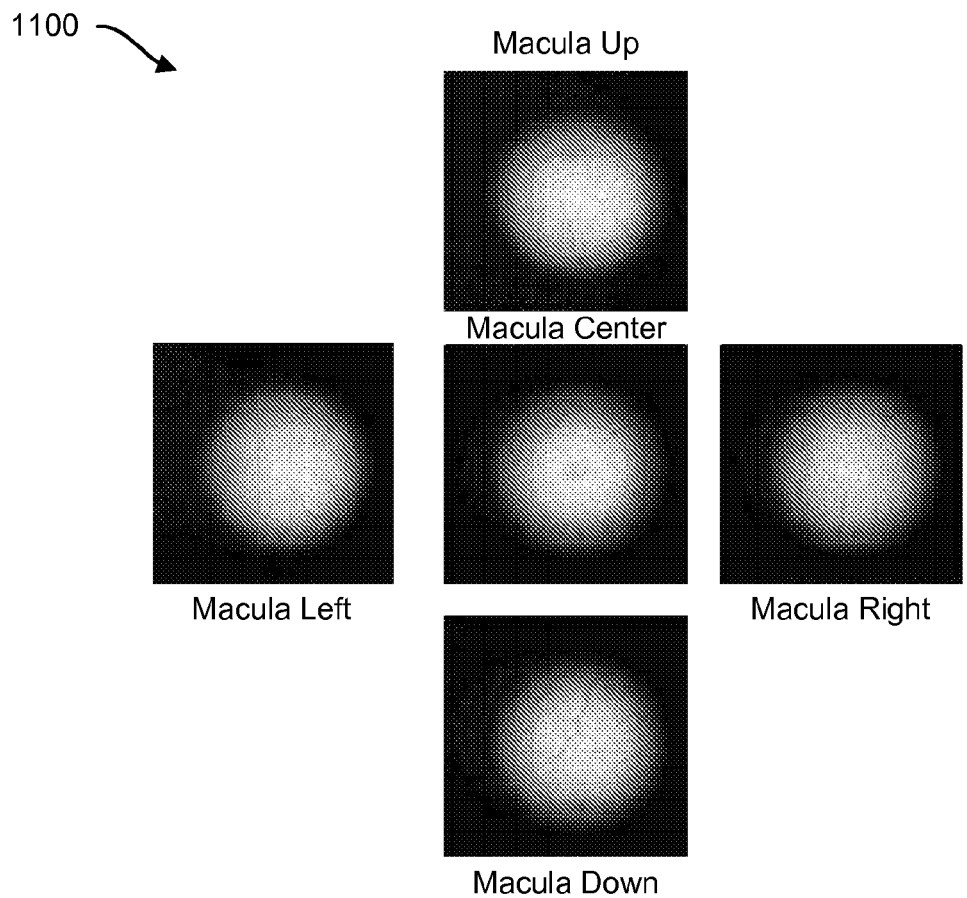
FIG. 11 illustrates retinal images obtained for optical detection of lipofuscin in the subject's eye from varying portions of the retina.
Figure 12:
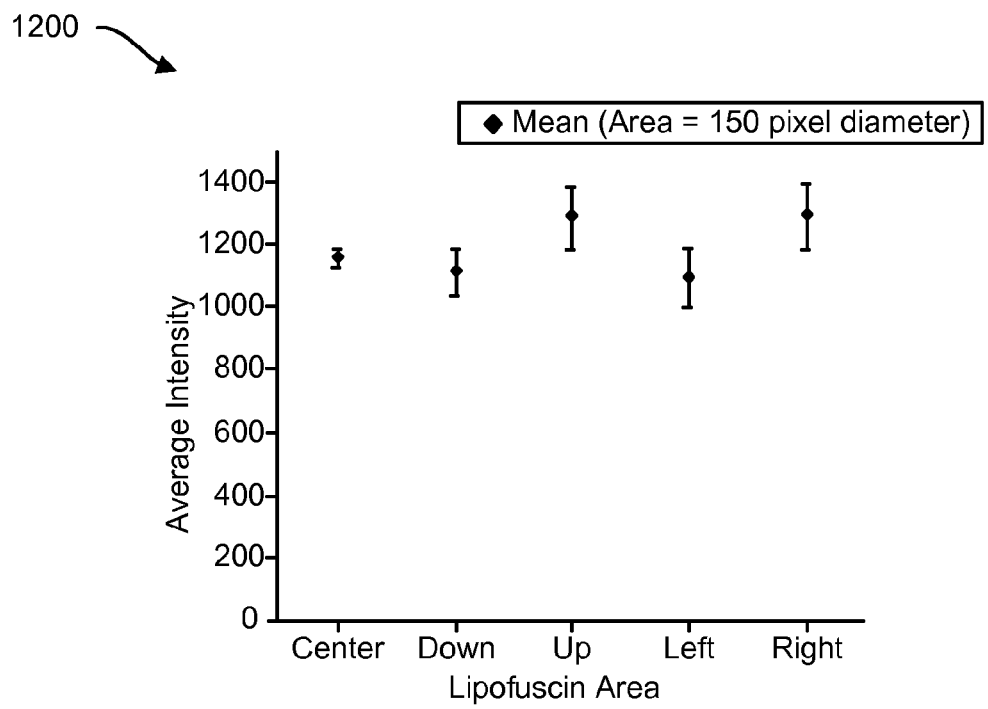
FIG. 12 illustrates a graph indicating the average intensity of lipofuscin levels in varied portions of the retina, corresponding to the images of FIG. 11.

FIG. 11 illustrates retinal images 1100 obtained for optical detection of lipofuscin in the subject's eye 404 from varying portions of the retina 405. FIG. 12 illustrates a graph 1200 indicating the average intensity of lipofuscin levels in varied portions of the retina 405. Referring to FIGS. 11 and 12, measurements of lipofuscin levels in five different areas of the retina 405 of a human volunteer subject's eye 404 were taken. The measurements were taken with a target 419 having a predetermined disk shape and a predetermined area of about 471 square pixels (i.e. a disk with a 150 pixel diameter). The light source for these measurements generated light at a wavelength of approximately 532 nm.

The measurements were taken from the macular region (Macula Center) and in off-macular regions. The off-macular regions included the temporal (Macula Right), nasal (Macula Left), superior (Macula Up) and inferior (Macula Down) positions, as shown in FIG. 11. Based on measurements of the average lipofuscin intensity in these various regions, the graph 1200 in FIG. 12 indicates the measured lipofuscin intensities in each position. Based on these results, the measured portions of the subject's retina 405 may be varied for optical detection of average lipofuscin levels.

Figure 13:
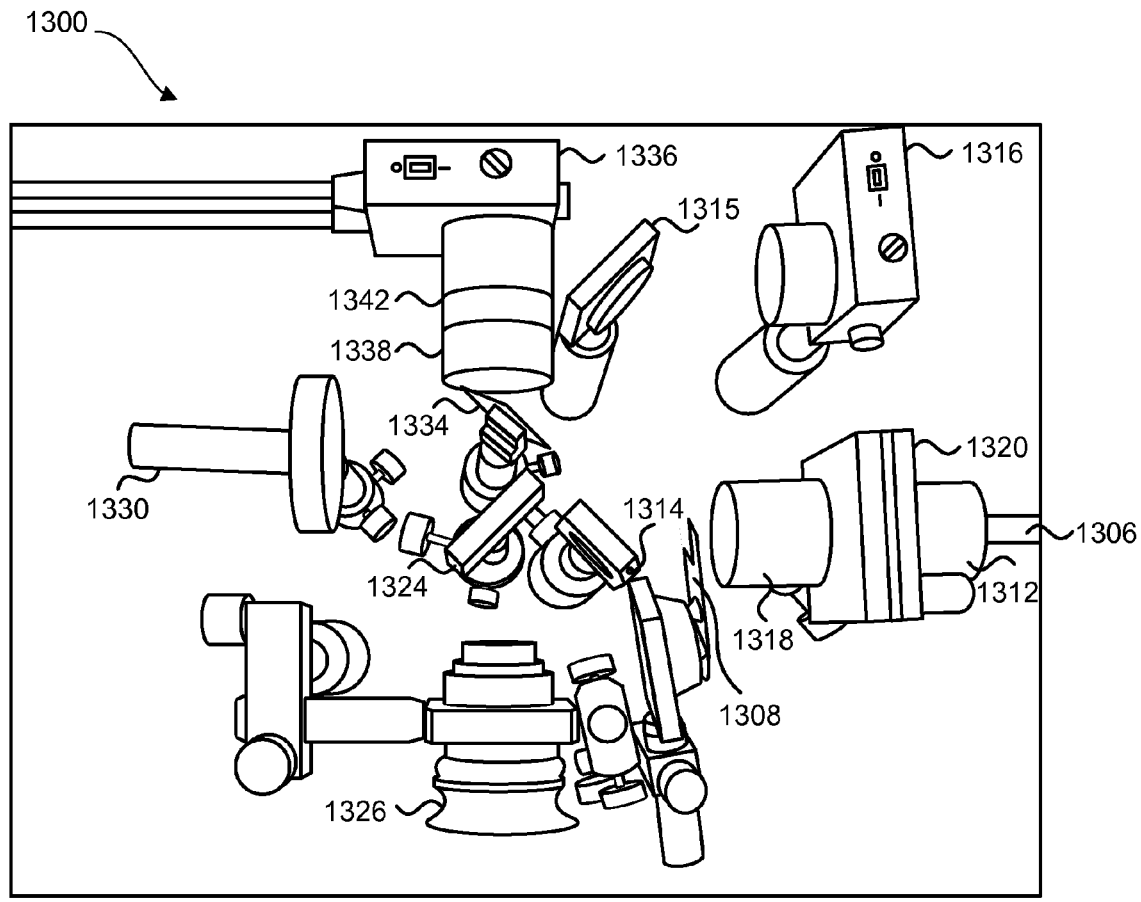
FIG. 13 is a block diagram of an embodiment of a system for optical detection of lipofuscin in a subject's eye.

FIG. 13 illustrates one embodiment of a system 1300 for optical detection of lipofuscin in a subject's retina 405. The system 1300 may include a light source (not shown). The light source may generate light that may be directed to a subject's eye/retina 404.

The light may be generated at a wavelength that substantially overlaps the absorption band of lipofuscin but does not substantially overlap the absorption band of macular carotenoids. In the present embodiment, the light source may be a bandwidth filtered LED light source.

The light source may be in optical communication with one or more optical components. The optical components may direct the light generated by the light source to the subject's eye 404. An optical fiber coupler 1306 may be used to direct the light generated by the light source. The light source may be in optical communication with a mechanical connector for fiber 1312.

The light may be communicated to an optics mount for excitation light fiber, collimator lens, filter, and beam expanding lens 1320. In the present embodiment, the optics mount 1320 may be a laser line filter. The light may be communicated to a beam expander and filter 1318. The beam expander and filter 1318 may condition the light to create a target 419. For example, the beam expander and filter 1318 may enlarge and/or reduce the light to a predetermined size and/or shape on the subject's retina 405. In the present embodiment, the beam expander and filter 1318 may expand the light to create about a 5 mm disk shaped target 419. In other embodiments, the beam expander and filter 1318 may expand and/or reduce the light to a target 419 with other predetermined shapes and/or areas. For example, the beam expander and filter 1318 may expand and/or reduce the light to predetermined shapes such as an ellipse, an annulus, a polygon, multiple ellipses and/or other predetermined shapes. In another example, the beam expander and filter 1318 may expand and/or reduce the light to predetermined areas such as about 157 square pixels, about 314 square pixels, about 471 square pixels, about 628 square pixels, and/or other predetermined areas.

The beam expander and filter 1318 may be used to direct the light into the subject's eye 404. In the present embodiment, the beam expander and filter 1318 may direct the shaped and/or sized light into the retina 405 of the subject's eye 404, the beam expander and filter 1318 may be positioned to direct the light into various portions of the subject's eye 404.

A mechanical shutter 1308 may be used to prevent optical communication between the generated light and the subject's eye 404. In the present embodiment, the shutter 1308 may be a mechanical shutter that may be controlled by a personal computer (not shown). The shutter 1308 may provide a light exposure time of about 200 msec.

The light may be communicated to a first beam splitter 1314. The first beam splitter 1314 may be positioned at an angle of incidence of about 45 degrees to the light source (i.e. to the light emitted from the light source). The first beam splitter 1314 may be used to direct a portion of the generated light to a first feedback detector 1316. The first feedback detector 1316 may be used for feedback control. A computing device may be in electronic communication with the first feedback detector 1316. In the present embodiment, a mirror 1315 may be in optical communication with the first beam splitter 1314 and/or the first feedback detector 1316. Mirrors 1315 may be used for optimal positioning of the various optical elements and to send excitation light to the feedback detector 1316.

The first beam splitter 1314 may direct another portion of the generated light to a second beam splitter 1324. In the present embodiment, the second beam splitter 1324 may be a dichroic holographic beam splitter. The second beam splitter 1324 may be used to reflect the light into the subject's eye 404.

The light may pass through an eye cup and aperture 1326 before contacting the subject's eye 404. The aperture 1326 may be positioned in front of the subject's eye 404. The aperture 1326 may be used to block reflections originating from the second beam splitter 1324. In some embodiments a chin rest (not shown) may be used to adjust the vertical position of the subject's eye 404.

An adjustable aiming beam generator 1330 (aiming light 1330) may be used to position the subject's eye 404. The aiming beam may be used to fixate the subject's eye 404. The adjustable aiming beam generator 1330 may be in optical communication with the subject's eye 404.

In the present embodiment, the adjustable aiming beam generator 1330 may be in optical communication with a third beam splitter 1334. The third beam splitter 1334 may be positioned at an angle of incidence of about 45 degrees to the subject's eye 404. The beam splitter 1334 may be used to couple the aiming beam into the instrument. The third beam splitter 1334 may reflect a fixation point 428 into the subject's eye 404. The fixation point 428, in the present embodiment, may pass through the second beam splitter 1324 and/or the aperture 1326 into the subject's eye 404. In the present embodiment, the subject's eye 404 may be fixated before the light is directed into the subject's eye 404. For example, the shutter 1308 may not activate until the subject's eye 404 is fixated.

The subject's eye 404 may be in optical communication with a second optical detector 1336. The second optical detector 1336 may be a photodetector for lipofuscin detection. A portion of the light may be absorbed by the subject's eye 404. A portion of the light may be emitted by the subject's eye 404. The portion of the light that may be emitted may pass through the aperture 1326. The emitted light may pass through the second beam splitter 1324. For example, the second beam splitter 1324 may be transparent for desired wavelengths. In the present embodiment, the second beam splitter 1324 may be a long pass filter at about 600 nm. The second beam splitter 1324 may be positioned at an angle of incidence of about 45 degrees to the light source (i.e. to the light emitted from the light source).

The emitted light may pass through the third beam splitter 1334. A second filter 1338 may be in optical communication with the subject's eye 404 and/or the second optical detector 1336. The second filter 1338 may be a notch filter used to prevent fluorescence emitted from the lens 440 of the subject's eye 404 from being detected by the second optical detector 1336. The second filter 1338 may further be used to prevent fluorescence from melanin in the subject's eye 404. In the present embodiment, the second filter 1338 may include a long pass filter at about 665 nm.

The second optical detector 1336 may detect the light emitted from the subject's eye 404. For example, the second optical detector 1336 may measure the intensity of the light emitted from the subject's eye 404. In the present embodiment, the second optical detector 1336 may be a photodetector for lipofuscin detection. The second optical detector 1336 may be sensitive in the red wavelength region generally.

A long-pass filter 1342 may be in optical communication with the second optical detector 1336 and/or the subject's eye 404. The long-pass filter 1342 may image the emitted light onto the second optical detector 1336.

The second optical detector 1336 may be in electronic communication with the computing device (not shown). The second optical detector 1336 may convert the detected light into an electronic signal. The electronic signal may be sent to the computing device. The computing device may be used to determine levels of lipofuscin in the subject's eye 404. Determining levels of lipofuscin in the subject's eye 404 may include processing the electronic signal from the second optical detector 1336. Processing the electronic signal from the second optical detector 1336 may include analyzing and/or visually displaying the signal on a monitor (not shown) and/or other display. Processing the electronic signal from the second optical detector 1336 may further include converting the light signal into other digital and/or numerical formats. Data acquisition software may be used by the computing device to determine the levels of lipofuscin in the subject's eye 404.

Figure 14:
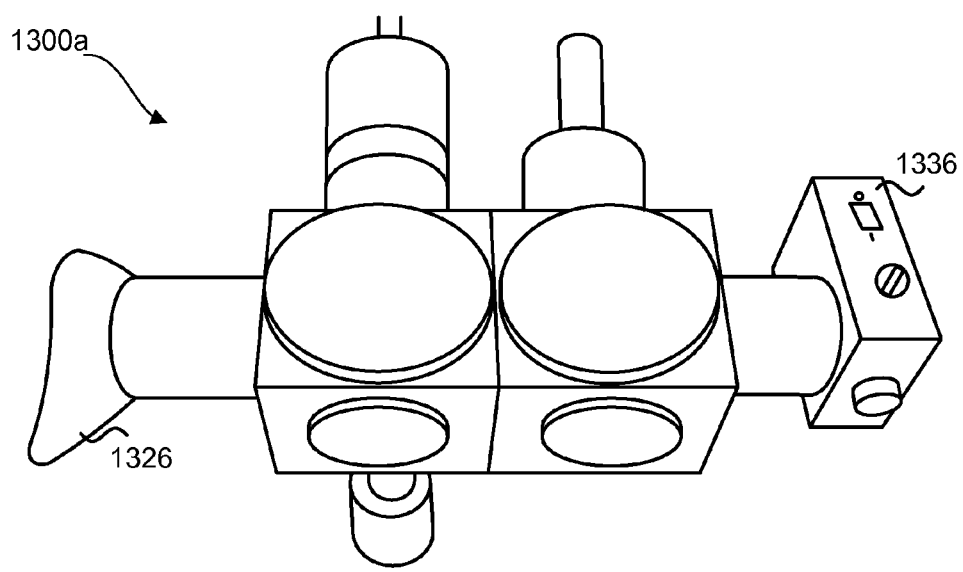
FIG. 14 illustrates an embodiment of an enclosed system corresponding to the block diagram of FIG. 13.

FIG. 14 illustrates an embodiment of an enclosed system 1300a for optical detection of lipofuscin in a subject's retina 405. The system 1300a of FIG. 14 corresponds to the open system 1300 shown in FIG. 13.

Figure 15:
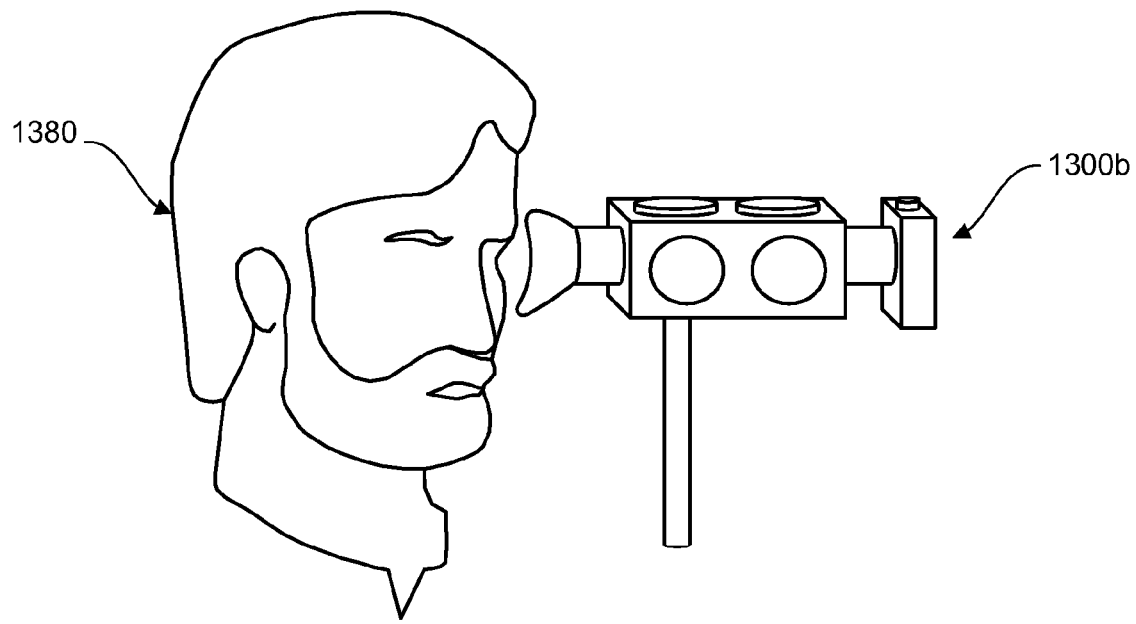
FIG. 15 illustrates a human subject using a system for optical detection of lipofuscin in the subject's retina.

FIG. 15 illustrates a human subject 1380 using a system 1300b for optical detection of lipofuscin in the subject's retina. The human subject 1380 positions the system 1300b such that the subject's eye is positioned by the eye cup and aperture 1326 so that the system 1300b may detect the lipofuscin levels in the human subject's retina.

Presently a camera is sold by KOWA, Inc. for high-resolution lipofuscin measurements. The present systems and methods are different from the Kowa camera for a number of reasons. Some of the differences are as follows. The Kowa camera is designed to record a high-resolution lipofuscin image of the retina. The objective is to provide physicians with an instrument that can look for any abnormalities from the usual, relatively even, distribution of lipofuscin. In some cases of retinal pathologies, spots or patterns with excessive lipofuscin concentrations can occur, and it is interesting for clinical researchers to try to study this phenomenon, and possibly link abnormal lipofuscin distributions to retinal diseases. The Kowa camera achieves its high spatial resolution by raster scanning a laser excitation beam across the retina, or by illuminating the whole hemisphere of the retina with light excitation, and by recording the images with a sensitive CCD camera. Besides the high spatial resolution, Kowa obtains with these approaches a very large field of view, effectively allowing the physician to see the whole retinal hemisphere. The physician can thus see besides the lipofuscin fluorescence, the influence of blood vessels, the optical nerve, the macular region, etc., on the images. The instrument is basically a highly complex, relatively expensive digital retinal camera, costing tens of thousands of dollars.

In comparison, the present systems and methods are quite different. The present systems and methods are not interested in a high-resolution lipofuscin image of the whole hemisphere, but instead in a spatially averaged lipofuscin concentration in healthy subjects. The purpose is to monitor the subject's lipofuscin levels over time as a function of supplements thought to decrease the lipofuscin levels. Lipofuscin measurements are accomplished with an extremely simple and inexpensive instrument configuration which sacrifices spatial resolution and field of view, but measures instead the lipofuscin levels in a representative area of the healthy retina. The present systems and methods achieve this in several ways, all minimizing the potentially confounding effects of other substances existing in the retina besides lipofuscin. The most important confounding substance is the macular pigment, which produces a strong yellow coloration in the macula region. To avoid its effect on the lipofuscin measurement, the present systems and methods use light excitation that is outside the absorption range of macular pigment (532 nm). In addition, the present systems and methods choose a retinal target area for measurement that is not centered on the macula, but instead located in the periphery. The light source the present systems and methods use is a simple "stationary", i.e. not raster-scanning, expanded, light beam. It is very inexpensive (non-laser), limits the measured area to a relatively small spot (~5 mm diameter instead of the whole hemisphere), but achieves the assessment of the lipofuscin levels in that area. The typical cost for a spatially averaging lipofuscin level instrument according to the present systems and methods may be very low compared to currently available lipofuscin detection schemes. Therefore, this instrument is well suited for use in the nutritional supplement industry.

Figure 16:
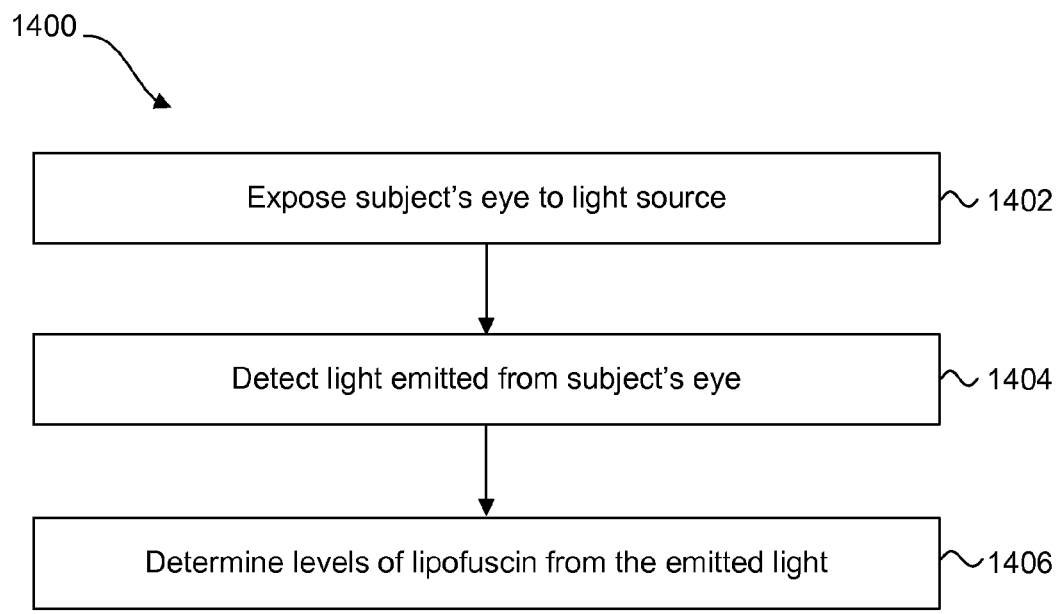
FIG. 16 is a flow diagram of an embodiment of a method for optical detection of lipofuscin in a subject's eye.

FIG. 16 is a flow diagram of an embodiment of a method 1400 for optical detection of lipofuscin in a subject's eye 404. The method 1400 may include exposing 1402 a subject's eye 404 to a light source 402. The light source 402 may be passed through one or more optical components.

Light emitted from the subject's eye 404 may be detected 1404. Detecting 1404 emitted light may include measuring the intensity of the light emitted from the subject's eye 404. The emitted light may be detected 1404 by an optical detector 416, 436 such as a CCD camera, a photomultiplier tube, a photodiode detector and/or other optical detector. Detecting 1404 emitted light may include converting the detected light into an electronic signal.

The levels of lipofuscin may be determined 1406 from the emitted light. Determining 1406 the levels of lipofuscin from the emitted light may include processing the electronic signal from an optical detector 416, 436. Processing the electronic signal from the optical detector 416, 436 may include analyzing and/or visually displaying the signal on a monitor and/or other display. Processing the electronic signal from the optical detector 416, 436 may further include converting the light signal into other digital and/or numerical formats. Data acquisition software may be used by the computing device to determine the levels of lipofuscin in the subject's eye 404.

The lipofuscin levels may be compared to correlative data indicative of one or more pathologies or symptoms. Based upon the comparison, the presence, absence, or degree of one or more pathologies or symptoms may be determined.

Figure 17:
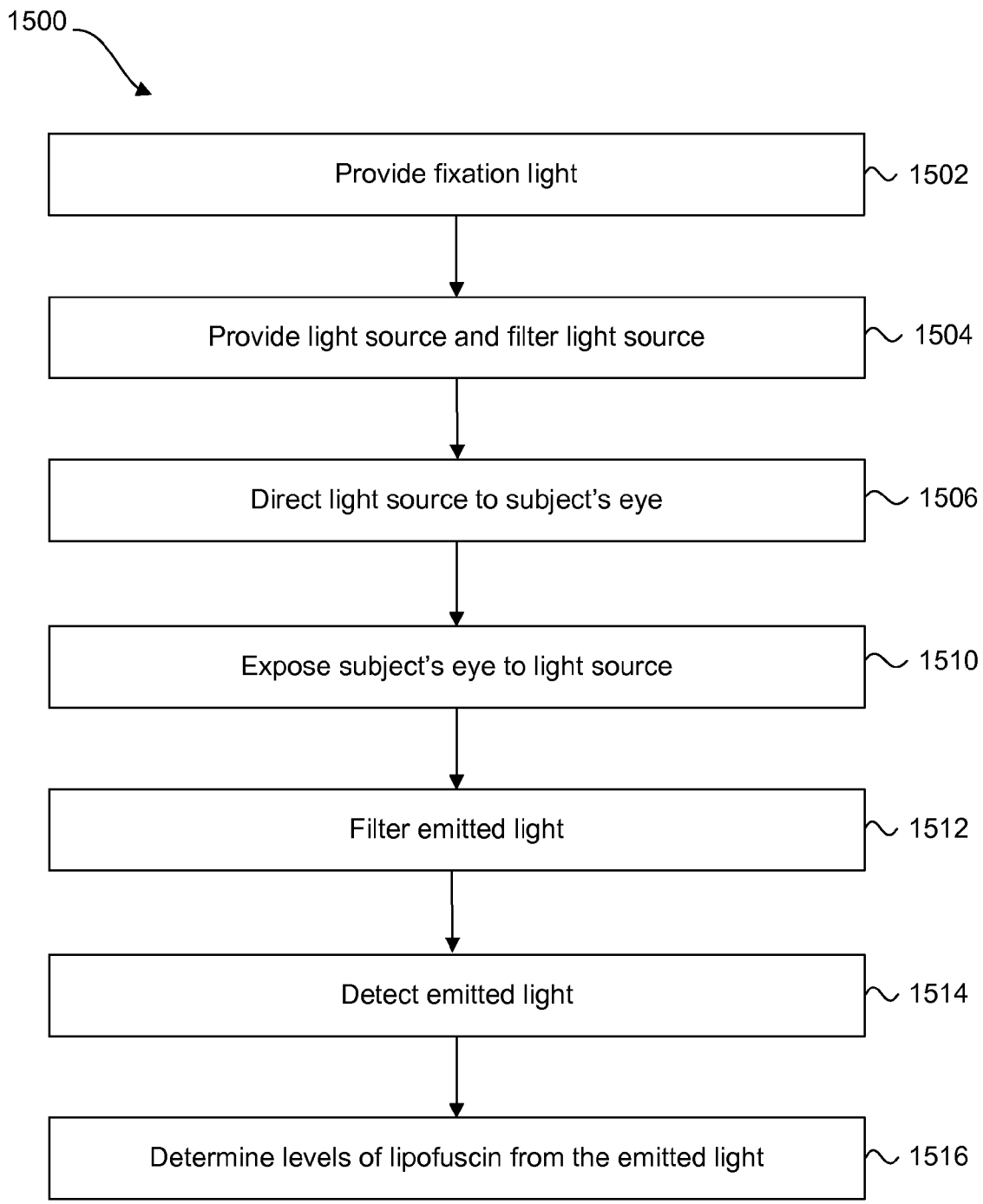
FIG. 17 is a more detailed flow diagram of the embodiment of a method for optical detection of lipofuscin in a subject's eye shown in FIG. 14.

FIG. 17 is a flow diagram of another embodiment of a method 1500 for optical detection of lipofuscin in a subject's eye 404. In the present embodiment, the method 1500 may include providing 1502 a fixation point 428. In some embodiments, the fixation point 428 may be provided 1502 by an adjustable aiming beam generator 430.

A light source 402 may be provided and filtered 1504. The light source 402 may be a coherent light source. The light source 402 may include a laser light source, an LED light source and/or other light sources. The light may be generated at a wavelength that substantially overlaps the absorption band of lipofuscin but does not substantially overlap the absorption band of macular carotenoids. In the present embodiment, the light may be generated at a wavelength of about 532 nm. In other embodiments, the light may be generated at wavelengths encompassing about 532 nm. In further embodiments, the light may be generated at wavelengths that may substantially overlap the absorption band of macular carotenoids. In embodiments where the light is generated at wavelengths that may substantially overlap the absorption band of macular carotenoids, the lipofuscin levels may be measured generally outside of the macular region.

The light generated by the light source 402 may be filtered 1504. Filtering 1504 the light generated by the light source 402 may include providing a narrow band pass filter, a laser line filter and/or another optical filter. Filtering 1504 the light generated by the light source 402 may include filtering the light to generally exclude light with wavelengths outside a desired band. For example, the light may be filtered 1504 to exclude wavelengths that are typically absorbed by macular pigments.

The light source 402 may be directed 1506 to the subject's eye 404. Directing 1506 the light source 402 to the subject's eye 404 may be accomplished using various optical elements. Directing 1506 the light source 402 to the subject's eye 404 may include conditioning the light to create a target 419. For example, a lens 418 may be used to expand the light to create about a 1 cm disk shaped target 419. In other embodiments, the light source 402 may be expanded and/or reduced to a target 419 with other predetermined shapes and/or areas.

The subject's eye 404 may be exposed 1510 to the light generated by the light source 402. In some embodiments, exposing 1510 the subject's eye 404 to the light generated by the light source 402 may include using a lens to direct the light source 402 into the retina 405 of the subject's eye 404. In further embodiments, exposing 1510 the subject's eye 404 to the light generated by the light source 402 may include exposing the subject's eye 404 to a target 419 with a predetermined shape and/or size.

The light emitted from the subject's eye 404 may be filtered 1512. Filtering 1512 the emitted light may include preventing fluorescence emitted from the lens 440 of the subject's eye 404. The melanin in the subject's eye 404 may be included in filtering 1512 the light emitted from the subject's eye 404. Filtering 1512 the emitted light may include providing a long pass filter. The long pass filter may filter at about 665 nm, 670 nm, 690 nm and/or other wavelengths.

The emitted light may be detected 1514. In the present embodiment, the emitted light may be detected 1514 by a photodiode detector. In other embodiments, the emitted light may be detected 1514 by a photomultiplier tube, a CCD camera and/or other optical detectors.

The levels of lipofuscin in the subject's eye 404 may be determined 1516 from the emitted light. Determining 1516 levels of lipofuscin in the subject's eye 404 may include processing the electronic signals from an optical detector 416, 436. Processing the electronic signal may include analyzing and/or visually displaying the signal on a monitor and/or other display. Processing the electronic signal may further include converting the light signal into other digital and/or numerical formats. Data acquisition software may be used to determine the levels of lipofuscin in the subject's eye 404.

In the present embodiment, one measurement (i.e. detection 1514) of the lipofuscin levels in the subject's eye 404 may be made. In other embodiments, multiple measurements may be taken. In embodiments where multiple measurements of lipofuscin levels may be taken, the multiple measurements may be averaged to determine an average lipofuscin level for the subject. In some embodiments where the lipofuscin levels may be averaged, the measurements may be taken from the same location in the subject's eye 404. For example, light used for each measurement may be directed to the same portion of the retina 405. In other embodiments, measurements may be taken from the different locations in the subject's eye 404. For example, light used for each measurement may be directed to the different portions of the retina 405. In further embodiments, a combination of measurements from the same and/or different locations may be used to determine the average lipofuscin levels in a subject's eye 404.

Figure 18:
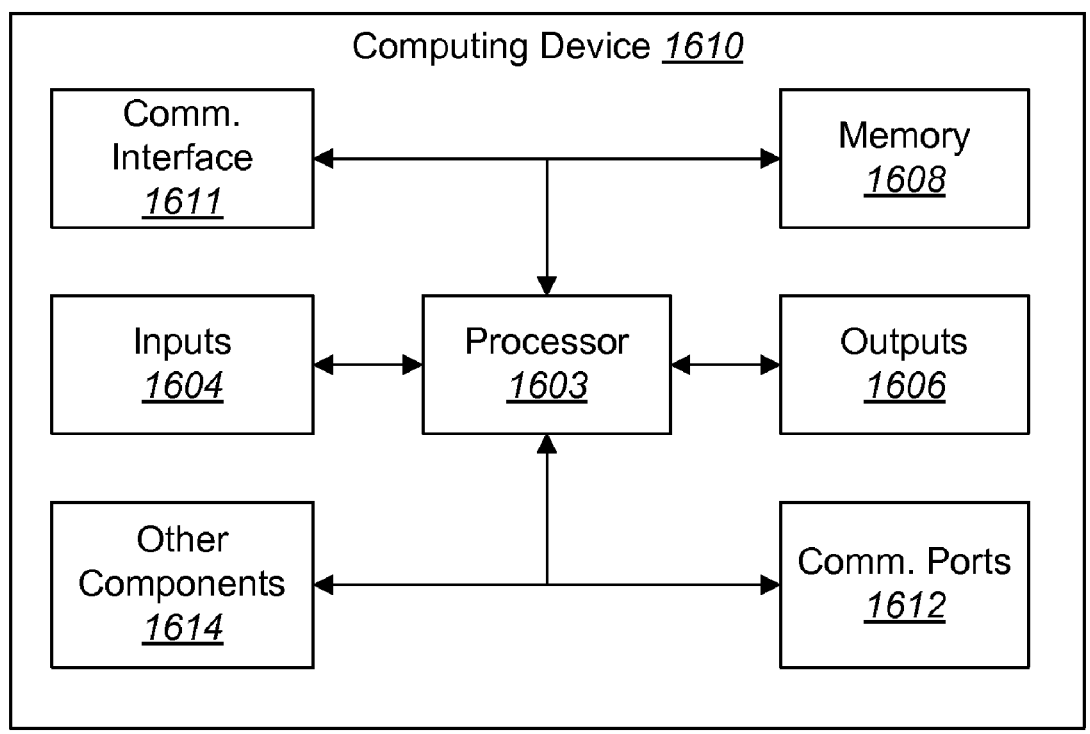
FIG. 18 is a block diagram illustrating various hardware components that may be used in an embodiment of a computing device.

FIG. 18 is a block diagram illustrating various hardware components that may be used in an embodiment of a computing device 1610. A computing device 1610 typically includes a processor 1603 in electronic communication with input components or devices 1604 and/or output components or devices 1606. The processor 1603 may be operably connected to input 1604 and/or output devices 1606 capable of electronic communication with the processor 1603, or, in other words, to devices capable of input and/or output in the form of an electrical signal. Embodiments of devices 1610 may include the inputs 1604, outputs 1606 and the processor 1603 within the same physical structure or in separate housings or structures.

The computing device 1610 may also include memory 1608. The memory 1608 may be a separate component from the processor 1603, or it may be on-board memory 1608 included in the same part as the processor 1603. For example, microcontrollers often include a certain amount of on-board memory. The memory 1608 may store information such as lipofuscin levels and/or other information that may be used with the present systems and methods.

The processor 1603 may also be in electronic communication with a communication interface 1611. The communication interface 1611 may be used for communications with other devices 1610. For example, the communication interface 1611 may be used to communicate with the optical detectors 416, 436 and/or the shutter 408. Thus, the communication interfaces 1611 of the various devices 1610 may be designed to communicate with each other to send signals or messages between computing devices 1610.

The computing device 1610 may also include other communication ports 1612. In addition, other components 1614 may also be included in the computing device 1610.

Many kinds of different devices may be used with embodiments herein. The computing device 1610 may be a one-chip computer, such as a microcontroller, a one-board type of computer, such as a controller, a typical desktop computer, such as an IBM-PC compatible, a Personal Digital Assistant (PDA), a Unix-based workstation, etc. Accordingly, the block diagram of FIG. 18 is only meant to illustrate typical components of a computing device 1610 and is not meant to limit the scope of embodiments disclosed herein.

Information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array signal (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The methods disclosed herein comprise one or more steps or actions for achieving the described method. The method steps and/or actions may be interchanged with one another without departing from the scope of the present invention. In other words, unless a specific order of steps or actions is required for proper operation of the embodiment, the order and/or use of specific steps and/or actions may be modified without departing from the scope of the present invention.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

What is claimed is:

1. A method for optical detection of lipofuscin concentrations in the retina, the method comprising:
    exposing a subject's eye to a light source, wherein the light source generates light at a wavelength that does not substantially overlap the absorption band of macular carotenoids, wherein the exposing comprises directing the light to an off-macular region of the subject's eye and not a macular region of the subject's eye, wherein the off-macular region is selected from the group consisting of a nasal portion, a temporal portion, a superior portion or an inferior portion;
    detecting light emitted from the subject's eye; and
    determining levels of lipofuscin from the emitted light.

2. The method of claim 1, further comprising exposing the subject's eye to a fixation point.

3. The method of claim 1, wherein detecting light emitted from the subject's eye further comprises filtering the light emitted from the subject's eye.

4. The method of claim 3, wherein filtering the light emitted from the subject's eye further comprises using a long pass filter at about 665 nm.

5. The method of claim 1, further comprising comparing the lipofuscin levels to correlative data indicative of changes of lipofuscin levels in a subject's eye over time due to the uptake of nutritional supplements or drugs.

6. A system for optical detection of lipofuscin concentrations in the retina, the system comprising:
    a light source to generate light, wherein the light generated by the light source is at a wavelength that substantially overlaps the absorption band of lipofuscin but does not substantially overlap the absorption band of macular carotenoids;
    an optical element to direct the light to an off-macular region of the subject's eye and not a macular region of the subject's eye, wherein the off-macular region is selected from the group consisting of a nasal portion, a temporal portion, a superior portion or an inferior portion;
    an optical detector in optical communication with the light source, the optical detector being configured to detect light emitted from a subject's eye; and
    a computing device in electronic communication with the optical detector, the computing device being configured to determine levels of lipofuscin from the emitted light.

7. The system of claim 6, wherein the light source generates light at a wavelength of about 532 nm.

8. The system of claim 6, further comprising an optical filter in optical communication with the optical detector and the subject's eye.

9. The system of claim 8, wherein the optical filter further comprises a long pass filter at about 665 nm.

10. A system for optical detection of lipofuscin concentrations in the retina, the system comprising:

a light source to generate light;

an optical element in optical communication with the light source, the optical element being configured to direct the light to an off-macular region of the subject's eye and not a macular region of the subject's eye, wherein the off-macular region is selected from the group consisting of a nasal portion, a temporal portion, a superior portion or an inferior portion;

an optical detector in optical communication with the light source, the optical detector being configured to detect light emitted from a subject's eye; and a computing device in electronic communication with the optical detector, the computing device being configured to determine levels of lipofuscin from the emitted light.

11. The system of claim 10, wherein the light generated by the light source is at a wavelength that substantially overlaps the absorption band of lipofuscin but does not substantially overlap the absorption band of macular carotenoids.

12. The system of claim 10, further comprising an optical filter in optical communication with the optical detector and the subject's eye.

13. The system of claim 12, wherein the optical filter further comprises a long pass filter at about 665 nm.

* * * * *